United States Patent [19]
Kuroda et al.

[11] Patent Number: 4,776,887
[45] Date of Patent: Oct. 11, 1988

[54] WAX AND INK COMPOSITION FOR THERMAL INK TRANSFER

[75] Inventors: Katsuhiko Kuroda, Yokohama; Hideki Yamanouchi, Machida; Tsutomu Baba, Hatano, all of Japan

[73] Assignee: Mitsubishi Chemical Industries Ltd., Tokyo, Japan

[21] Appl. No.: 23,903

[22] Filed: Mar. 10, 1987

Related U.S. Application Data

[63] Continuation of Ser. No. 712,100, Mar. 15, 1985, abandoned.

[30] Foreign Application Priority Data

Mar. 22, 1984 [JP] Japan .................................. 59-54941
Oct. 3, 1984 [JP] Japan ................................ 59-207360

[51] Int. Cl.$^4$ ............................................. C09D 11/12
[52] U.S. Cl. ...................................... 106/31; 106/272
[58] Field of Search ................................. 106/31, 272

[56] References Cited

U.S. PATENT DOCUMENTS

| | | | |
|---|---|---|---|
| 3,235,526 | 2/1966 | Williams | 524/549 |
| 3,249,454 | 5/1966 | Williams | 106/309 |
| 3,249,455 | 5/1966 | Williams | 106/309 |
| 3,322,713 | 5/1967 | Williams | 524/549 |
| 3,687,887 | 8/1972 | Zabiak | 524/104 |
| 3,991,032 | 11/1976 | Pace | 524/549 |
| 4,071,581 | 1/1978 | Yokoyama | 526/56 |
| 4,244,866 | 1/1981 | Schefbauer | 106/28 |
| 4,320,046 | 3/1982 | Havens | 524/83 |
| 4,358,573 | 11/1983 | Verbrugge | 526/272 |

FOREIGN PATENT DOCUMENTS

| | | |
|---|---|---|
| 0024034 | 2/1981 | European Pat. Off. . |
| 1337724 | 11/1973 | United Kingdom . |
| 1398000 | 6/1975 | United Kingdom . |
| 2006793 | 5/1979 | United Kingdom . |
| 2068386 | 8/1981 | United Kingdom . |

Primary Examiner—Amelia Burgess Yarbrough
Attorney, Agent, or Firm—Oblon, Fisher, Spivak, McClelland & Maier

[57] ABSTRACT

A wax for thermal ink transfer, which consists essentially of a reaction product of an α-olefin having an average carbon number of from 16 to 100 with maleic anhydride, said reaction product having a weight average polymerization degree of from 1 to 100 and which has a heat of fusion of not higher than 40 cal/g.

21 Claims, No Drawings

WAX AND INK COMPOSITION FOR THERMAL INK TRANSFER

This application is a continuation of application Ser. No. 712,100, filed on Mar. 15, 1985, now abandoned.

BACKGROUND OF THE INVENTION

1. Field of the Invention

The present invention relates to a wax for thermal ink transfer, and an ink composition comprising such a wax and a coloring matter.

2. Description of the Prior Art

In recent years, there have been remarkable developments in thermal ink transfer type printers or facsimiles by virtue of their merits such as simplicity in handling and low costs. In such printers or facsimiles, it is common to employ a thermal ink transfer type recording medium in the form of a ribbon or sheet, which comprises a substrate and a thermal transfer ink coated thereon and composed essentially of a wax and a coloring agent.

The thermal ink transfer type recording medium is so designed that when pressed with a heating element such as a thermal head, the thermal transfer ink layer is melted and transferred in the pattern of a heat-pressed image onto a paper sheet to form a record. Thus, the properties of the thermal transfer ink, particularly the properties of the wax as an essential component of the ink, affect the performance of the recording system to a large extent.

As such a wax, there have been used natural waxes such as carnauba wax, montan wax, Japan wax, beeswax, ceresin wax and spermaceti, and synthetic waxes such as petroleum wax, low molecular weight polyethylene and oxidized wax.

However, in the conventional thermal transfer inks using these waxes, the dispersibility of the pigment was inadequate. Further, they had drawbacks such that the heat of fusion was as high as at least about 40 cal/g, and the thermal shrinkage was relatively great, whereby the printed images tended to be unclear, and the printing speed was slow because a substantial energy was required for the melting of the ink layer.

The present inventors have conducted extensive research with an aim to develop a wax suitable for thermal ink transfer, and have finally accomplished the present invention.

SUMMARY OF THE INVENTION

It is an object of the present invention to provide an ink composition for thermal ink transfer, which is useful for thermal ink transfer type recording materials.

Another object of the present invention is to provide a wax particularly useful for an ink composition for thermal ink transfer.

The present invention provides, in the broadest sense, a wax for thermal ink transfer, which consists essentially of a reaction product of an α-olefin having an average carbon number of from 16 to 100 with maleic anhydride, said reaction product having a weight average polymerization degree of from 1 to 100 and which has a heat of fusion of not higher than 40 cal/g.

The present invention also provides an ink composition for thermal ink transfer, which comprises a coloring matter and the wax as defined above.

Further, a thermal ink transfer type recording material is constituted by a combination of the above ink composition with a proper substrate.

DETAILED DESCRIPTION OF THE INVENTION

The wax for thermal ink transfer according to the present invention consists essentially of a reaction product of an α-olefin having an average carbon number of from 16 to 100 with maleic anhydride, having a weight average polymerization degree of from 1 to 100, and has a heat of fusion of not higher than 40 cal/g. As the α-olefin, there may be employed olefins having an average carbon number of from 16 to 100 with a double bond at the α-position. The α-olefin may be a single substance or a mixture of a plurality of α-olefins having different numbers of carbon atoms.

If an α-olefin having an average carbon number of less than 16 is employed, the resulting product tends to be poor in the properties as wax. On the other hand, if the average carbon number exceeds 100, the heat of fusion of the resulting wax tends to be too high. In either case, the resulting product will not be suitable as a wax for an ink composition for thermal ink transfer.

As the reaction product of the α-olefin with maleic anhydride, there may be mentioned a copolymer of the α-olefin with maleic anhydride, a 1:1 adduct of the α-olefin with maleic anhydride, with a mixture thereof.

In the case of a copolymer, the α-olefin preferably has a carbon number of from 16 to 60, more preferably from 22 to 60, within the above-mentioned range of the average carbon number of from 16 to 100. If the average carbon number exceeds 60, the melting point tends to be high.

The copolymerization reaction of the α-olefin with maleic anhydride may be conducted in a usual manner by a solution polymerization or solventless (bulk) polymerization in the presence of a radical catalyst.

In the solution polymerization, xylene, toluene, benzene or the like is used as the solvent. The polymerization is conducted usually at a temperature of from 60° to 140° C. for 3 to 8 hours. After the completion of the polymerization reaction, the solvent, unreacted α-olefin and maleic anhydride are separated from the reaction mixture by distillation, whereby the desired copolymer can readily be obtained.

On the other hand, it is advantageous to employ a solventless copolymerization method to increase the productivity. However, in this case, it is necessary to properly control the polymerization degree by using a proper radical transfer agent or by increasing the polymerization temperature. As such a radical transfer agent, there may be mentioned lauryl mercaptan, stearyl mercaptan or p-t-butylphenol. Such a radical transfer agent is added usually in the amount of from 1/100 to 1/10 mol per mol of maleic anhydride. Alternatively, without using such a radical transfer agent, it is possible to obtain a copolymer having a proper polymerization degree by simply increasing the polymerization temperature to a level of from 160° to 200° C. In this case, as a method for obtaining a copolymer having a good hue, it is effective to employ a method wherein maleic anhydride is continuously supplied to the α-olefin during the copolymerization reaction.

After the completion of the reaction, the unreacted α-olefin and maleic anhydride are removed by distillation under reduced pressure, whereby the desired copolymer is readily obtained.

The wax for thermal ink transfer thus consisting essentially of a copolymer of the α-olefin and maleic anhydride, provides good dispersibility for pigments and has an excellent hue. The heat of fusion is low, and the thermal shrinkage is minimum. Thus, it has excellent basic properties as a wax for thermal transfer inks.

Whereas the 1:1 adduct of an α-olefin with maleic anhydride corresponds to a reaction product of the α-olefin with maleic anhydride with a weight average polymerization degree of 1. (The weight average polymerization degree will be defined hereinafter.) In this case, the α-olefin has an average carbon number of from 16 to 100, preferably from 16 to 60, more preferably from 22 to 60. Such an adduct may be obtained in a usual manner by heating the α-olefin and maleic anhydride at a temperature of from 160° to 260° C., preferably from 180° C. to 250° C., more preferably from 190° to 230° C., in the absence of a solvent.

After the completion of the reaction, the unreacted α-olefin and maleic anhydride are removed by distillation under reduced pressure, whereby the desired adduct is obtained.

The 1:1 thermal addition reaction product of the α-olefin with maleic anhydride, i.e, an alkenyl succinic anhydride, has a lower melt viscosity than the above-mentioned copolymer. Accordingly, the operation efficiency for melting the wax or the coating property of the ink onto the substrate can further be improved by incorporating this alkenyl succinic anhydride into the wax component.

The above-mentioned reaction for the formation of the copolymer of the α-olefin with maleic anhydride is represented by the following formula I, wherein R is an alkyl group having an average carbon number of from 13 to 97, and $m \geq 1$.

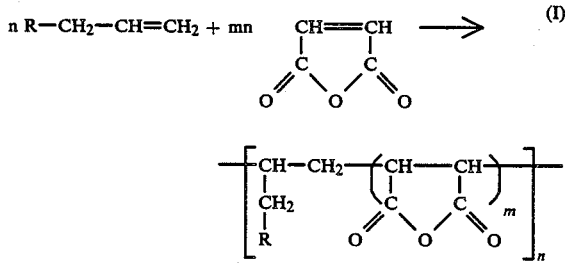

The reaction for the formation of the 1:1 adduct of the α-olefin with maleic anhydride, i.e. the alkenyl succinic anhydride, corresponding to the weight average polymerization degree of 1, is represented by the following formula II, wherein R is as defined above.

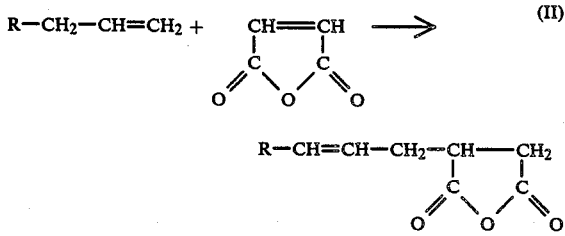

As mentioned above, the alkenyl succinic anhydride is obtained by subjecting an α-olefin and maleic anhydride to a thermal addition reaction. However, in the thermal addition reaction product, maleic anhydride and the α-olefin remain as unreacted materials. It is likely that a part of the remaining maleic anhydride undergoes thermal decomposition or forms by-products, whereby the product tends to be colored, or the quality of the product deteriorates.

In order to avoid such drawbacks, it is advantageous to use a reaction product of the α-olefin with maleic anhydride, which is obtained by subjecting the α-olefin and maleic anhydride to a thermal addition reaction, followed by a radical reaction with an addition of a peroxide, whereby the unreacted olefin and maleic anhydride are reacted. The reaction product thereby obtained is a mixture comprising the alkenyl succinic anhydride and the α-olefin-maleic anhydride copolymer as the main components, whereby the essential desirable properties of the alkenyl succinic anhydride are maintained without change and yet the remaining maleic anhydride is substantially minimized. When this product is used as a wax component, the hue and quality of the wax product will be improved, and the coating property of the ink composition onto the substrate will be improved. Namely, even when the substrate such as a sheet is made thin to improve the transfer efficiency, wrinkles or curling will scarcely form after the coating.

In this case, the α-olefin has an average carbon number of from 16 to 100, preferably from 16 to 60, more preferably from 22 to 60. Particularly preferred is a mixture of α-olefins having from 16 and 18 carbon atoms, a mixture of α-olefins having from 20 to 28 carbon atoms or a mixture of α-olefins having from 30 to 60 carbon atoms, which is obtained from the polymerization of ethylene.

The thermal addition reaction is conducted usually at a temperature of from 160° to 260° C., preferably from 180° to 250° C., more preferably from 190° to 230° C. The reaction time is usually from 30 minutes to 24 hours, preferably from 2 to 12 hours. The molar ratio of the α-olefin to maleic anhydride to be charged, is usually from 1:0.5 to 1:2, preferably from 1:1 to 1:2. The reaction is usually conducted in the absence of a solvent until not higher than 95 mol%, preferably from 30 to 95 mol%, more preferably from 60 to 90 mol%, of maleic anhydride is reacted, and then the reaction system is cooled to terminate the thermal addition reaction.

Then, a peroxide is added, whereby the unreacted maleic anhydride undergoes radical reaction.

The peroxide to be added to the thermal addition reaction product may be any usual radical forming agent. For instance, di-t-butylperoxide, t-butylhydroperoxide or the like is added in an amount of from 0.001 to 0.1 mol% relative to the α-olefin as initially charged.

The temperature for the radical reaction of the remaining maleic anhydride f by the addition of the peroxide, is usually from 100° to 260° C., preferably from 130° to 200° C. The unreacted maleic anhydride is substantially reacted usually in from 30 minutes to 10 hours.

The alkenyl succinic anhydride-containing composition thus obtained, is a mixture comprising a 1:1 adduct of the α-olefin with maleic anhydride and the copolymer of the α-olefin with maleic anhydride. The ratio of the 1:1 adduct to the copolymer roughly corresponds to the ratio of the thermal addition reaction rate to the radical reaction rate. The melting point of the product is usually from 30° to 95° C., and the viscosity at 100° C. is usually from 10 to 1000 cp. In particular, when a straight chain α-olefin having at least 28 carbon atoms is used, the melting point will be from 55° to 95° C., and the viscosity at 100° C. will be from 30 to 150 cp. The unreacted maleic anhydride remaining in the reaction product is usually not higher than 3% relative to the charged amount. In the case where only the thermal addition reaction is conducted, a substantial amount of unreacted maleic anhydride remains, which causes a trouble during the purification operation, or if the reaction is conducted at a higher temperature for a long period of time to reduce the amount of the unreacted maleic anhydride, the product tends to deteriorate. Whereas, by the combination of the thermal addition reaction with the subsequent radical reaction, no substantial amount of unreacted maleic anhydride remains, whereby no trouble during the purification operation is brought about. Further, the hue and quality of the product are improved. Thus, the product adequately satisfies the above-mentioned properties required for the wax for a thermal transfer ink.

The molar ratio of the α-olefin to the maleic anhydride in the reaction product obtained by the above mentioned various reactions between the α-olefin and maleic anhydride, is usually within a range of from 1:1 to 1:2.

In the present invention, among the reaction products of α-olefins with maleic anhydride, those having a weight average polymerization degree of from 1 to 100 are used. The weight average polymerization degree is determined by the following method.

Method for measuring a weight average polymerization degree ($P_w$)

The weight average polymerization degree is calculated by the following equation by means of a calibration curve for standard polystyrene by gel permeation chromatography (G.P.C.).

$$P_w = \frac{\Sigma NiPi^2}{\Sigma NiPi}$$

Where:
$P_w$: Weight average polymerization degree
Ni: Number of molecules i
Pi: Polymerization degree (n) of molecules i (The polymerization degree corresponds to the numerical value n in the foregoing reaction formula I.)

If the weight average polymerization degree is too high, the melt viscosity becomes too high to obtain satisfactory printing properties. Thus, the weight average polymerization degree is usually within a range of from 1 to 100, preferably from 1 to 40.

Further, among the reaction products of α-olefins with maleic anhydride, those having a heat of fusion of not higher than 40 cal/g are used from the view points of the recording sensitivity and recording speed of the thermal ink transfer recording media.

The reaction product of the α-olefin with maleic anhydride thus obtained can be used as a wax for thermal ink transfer in the same way as the conventional wax, i.e. by blending it with a coloring matter and optional plasticizer to form a thermal transfer ink. Then, the thermal transfer ink is coated on a substrate to obtain a thermal ink transfer recording material.

It is of course possible to use a conventional wax in combination with the wax of the present invention for the preparation of a thermal transfer ink to such an extent that the conventional wax does not impair the desirable properties of the wax of the present invention. In such a case, it is usual that the wax of the present invention is used in an amount of at least 5% by weight, preferably at least 10% by weight, more preferably at least 20% by weight, based on the wax component used, although the amount may vary depending upon the particular purpose.

Thus, the ink composition for thermal ink transfer according to the present invention comprises usually from 5 to 30% by weight, preferably from 10 to 20% by weight, of a coloring matter such as a pigment or dyestuff and from 70 to 95% by weight, preferably from 80 to 90% by weight, of a wax component, wherein the wax component comprises from 5 to 100% by weight, preferably from 10 to 100% by weight, more preferably from 20 to 100% by weight, of the wax of the present invention and from 0 to 95% by weight, preferably from 0 to 90% by weight, more preferably from 0 to 80% by weight, of a conventional wax, e.g. a natural wax such as paraffin wax, carnauba wax, montan wax, Japan wax, beeswax, ceresin wax, candelilla wax or spermaceti, or a synthetic wax such as petroleum wax, law molecular weight polyethylene or oxidized wax. Further, the wax component may contain from 0 to 50% by weight, preferably from 0 to 20% by weight, of a commonly used additive such as a plasticizer.

The distinction of the wax of the present invention over the conventional waxes is that the conventional waxes are all made of straight chain molecules, whereas the wax of the present invention has alkyl side chains attached, like teeth of a comb, to the principal chain, and it has polar groups consisting of the residues of maleic anhydride. Thus, the wax of the present invention is a wax having a totally new structure. By virtue of the peculiarity in the chemical structure, the wax of the present invention has the following extremely useful properties as a wax for thermal ink transfer, as compaired with the conventional waxes: (1) the dispersibility of pigments is extremely high, (2) the heat of fusion and thermal shrinkage are low, and (3) the hue is good.

Namely, as the dispersibility of pigments is high, it is possible to disperse a coloring matter such as carbon black uniformity in a high concentration under an extremely stable condition, and yet it is possible to obtain an extremely clear printing image. Further, as the heat of fusion is low as compaired with the conventional wax, the ink transfer can be conducted with a low energy consumption, and it is possible to increase the printing speed, whereby a thermal ink transfer recording medium having a high sensitivity can be obtained. Furthermore, as the heat shrinkage is small, it is possible to minimize the formation of curling or wrinkles due to the thermal shrinkage of the ribbons or sheets coated with the thermal transfer ink composition, whereby a clear printing image is obtainable.

Now, the present invention will be described in further detail with reference to Examples. However, it should be understood that the present invention is by no means restricted by these specific Examples.

In the Examples, the weight average polymerization degree was measured under the following conditions by means of high speed liquid chromatography HLC-802 UR, manufactured by Toyo Soda Manufacturing Co., Ltd.

Solvent: THF (tetrahydrofuran)
Column: 4000, 3000, 2000×2 (columns manufactured by Toyo Soda Manufacturing Co., Ltd.)
Temperature: 40° C.
Flow rate: 1.2 ml/min

Production Example 1 (Production of an α-olefin-maleic anhydride copolymer)

Into a flask, 1200 g of a mixture of α-olefins having from 30 to 60 carbon atoms (average carbon number of 48; DIALEN 30 (trademark) manufactured by Mitsubishi Chemical Industries, Ltd.) was charged, and after thoroughly flushing with nitrogen gas, heated to 185° C. Then, 180 g of maleic anhydride and 4.55 g of di-t-butylperoxide were simutaneously supplied thereto over a period of 2 hours under stirring, whereby the polymerization was conducted. After aging for further 1 hour, the reaction mixture was cooled to obtain 1370 g of an α-olefin-maleic anhydride copolymer (Reaction Product I). Its average molecular weight was 9260 as measured by G.P.C. method. The properties of this reaction product are shown in Table 1 together with the properties of carnauba wax, beeswax and paraffin wax.

Production Example 2 (Production of an α-olefin-maleic anhydride copolymer)

Into a flask, 650 g (1 mol) of a mixture of α-olefins having from 30 to 60 carbon atoms (DIALEN 30) and 98 g (1 mol) of maleic anhydride were charged, and after thoroughly flushing with nitrogen gas, heated to 180° C. Then, 8.76 g (0.06 mol) of di-t-butylperoxide was added over a period of 2 hours while paying due attention to the heat generation, whereby the radical copolymerization was conducted. After the completion of the addition, the reaction system was maintained at 180° C. for 1 hour to complete the reaction, whereby an α-olefin-maleic anhydride copolymer (Reaction Product II) was obtained. The conversion of the maleic anhydride in this reaction was at least 98%. The hue was good, and the reaction product was useful as a final product without any further purification. The physical properties of the reaction product are shown in Table 1.

Production Example 3 (Production of an α-olefin-maleic anhydride adduct)

Into a flask, 600 g of a mixture of α-olefins having from 20 to 28 carbon atoms (average carbon number of 23; DIALEN 208 (trademark) manufactured by Mitsubishi Chemical Industries, Ltd.), 600 g of a mixture of α-olefins having from 30 to 60 carbon atoms (the same as the mixture of α-olefins used in Production Example 1) and 311 g of maleic anhydride were charged, and after thoroughly flushing with nitrogen gas, heated to 200° C. under stirring and then reacted at the same temperature for 8 hours under stirring. Then, while gradually reducing the pressure, unreacted maleic anhydride was distilled off to obtain 140 g of a 1:1 adduct of the α-olefins with maleic anhydride (Reaction Product III). The physical properties of the reaction product are shown in Table 1.

Production Example 4 (Production of an α-olefin-maleic anhydride adduct)

Into a flask, 650 g (1 mol) of a mixture of α-olefins having from 30 to 60 carbon atoms (DIALEN 30) and 98 g (1 mol) of maleic anhydride were charged, and after thoroughly flushing with nitrogen gas, reacted at a temperature of 200° C. for 6 hours and then at a temperature of 220° C. for further 2 hours. The conversion of the maleic anhydride in this reaction was 85%. Then, it was attempted to distil off maleic anhydride under reduced pressure, whereby the piping for distillates was clogged with maleic anhydride. Therefore, the piping was heated and kept warm while maleic anhydride was distilled off, whereby an alkenyl succinic anhydride (Reaction Product IV) was obtained. The product was heavily colored, and insoluble colored substances deposited on the reactor and precipitated at the lower portion of the product. The physical properties of the reaction product are shown in Table 1.

Production Example 5

Into a flask, 650 g (1 mol) of a mixture of α-olefins having from 30 to 60 carbon atoms (straight chain α-olefins obtained by the polymerization reaction of ethylene; DIALEN 30 (trademark) manufactured by Mitsubishi Chemical Industries, Ltd.) and 98 g (1 mol) of maleic anhydride were charged, and after thoroughly flushing with nitrogen gas, reacted at a temperature of 200° C. for 4 hours. The conversion of the maleic anhydride in this reaction was 70%. Then, the reaction mixture was gradually cooled to a temperature of 170° C. and 1.46 g (0.01 mol) of di-t-butylperoxide was added thereto. The mixture was maintained and reacted at 170° C. for 1 hour, whereby a composition containing an alkenyl succinic anhydride (Reaction Product V) was obtained. The conversion of maleic anhydride in this reaction was at least 99%. No substantial colored by-products were present, and the hue was good. The reaction product was useful as a final product without any purification. The physical properties of the reaction product are shown in Table 1.

TABLE 1

|  | Viscosity[*1] (cp) | Hue[*2] (Gardner) | Needle penetration[*3] (1/10 mm) | Melting point[*4] (°C.) | Heat of fusion[*5] (cal/g) | Shrinkage[*6] (%) | Dispersibility of pigment[*7] |
|---|---|---|---|---|---|---|---|
| Reaction Product I | 160 | 2 | — | 74–76 | 20 | 12.0 | A |
| Reaction Product II | 200 | 2–3 | 3 | 74–76 | 20 | 12.0 | A |
| Reaction Product III | 36 | 7 | — | 56 | 18 | 11.5 | A |
| Reaction Product IV | 40 | 17–18 | 5 | 72–76 | 35 | 14.8 | A |
| Reaction Product V | 50 | 9–10 | 2–3 | 72–76 | 33 | 14.5 | A |
| Carnauba wax | 30 | 7–8 | <1 | 80–86 | 48 | 19.5 | C |
| Bees Wax | 9 | 1 | 17 | 62–65 | 42 | 16.0 | B |
| Paraffin | 5 | <1 | 11 | 68–69 | 60 | 20.0 | C |

TABLE 1-continued

|  | Viscosity*1 (cp) | Hue*2 (Gardner) | Needle penetration*3 (1/10 mm) | Melting point*4 (°C.) | Heat of fusion*5 (cal/g) | Shrinkage*6 (%) | Dispersibility of pigment*7 |
|---|---|---|---|---|---|---|---|
| wax (155° F.) | | | | | | | |

*1Viscosity: Measured at 100° C. by means of B-Model Viscometer manufactured by Tokyo Keiki Seizosho K.K.
*2Hue: Measured at 100° C. in accordance with ASTM D-1544.
*3Needle penetration: Measured at 25° C. in accordance with ASTM D-1321-61T.
*4Melting point: Measured by means of an automatic melting point measuring apparatus (METTLER FP manufactured by METTLER INSTRUMENTE AG)
*5Heat of fusion: Measured by means of a Differential Scanning Calorimeter (DSC-20 Model, manufactured by Seiko Instruments & Electronics Ltd.)
*6Shrinkage: The volume shrinkage when cooled from 125° C. to 25° C., was measured.
*7Dispersibility of pigment: 2.5 g of each wax was added to 19 g of spindle oil, and the mixture was introduced into a 500 ml round bottom flask, heated to a temperature of from 95 to 100° C., stirred and dissolved. Then, 3.5 g of carbon black and 20 g of glass beads having a diameter of 3 mm were added thereto. The mixture was stirred at a temperature of from 95 to 100° C. for 30 minutes to obtain a test ink. One drop of this test ink was dropped on a glass sheet heated to 95° C., and after covering with a cover glass, observed and evaluated by a microscope with 200 magnifications. The evaluation standards are shown below.
Evaluation Standard
A: No coagulation is observed even when no pressure is imparted to the cover glass.
B: Coagulations are observed when no pressure is exerted to the cover glass, although the coagulations disappear when a predetermined pressure is exerted to the cover glass.
C: Coagulations are observed even when a predetermined pressure is exerted to the cover glass.

It is evident from Table 1 that the waxes of the present invention have extremely useful properties for an ink composition for thermal ink transfer, i.e. a low heat of fusion, low shrinkage and high dispersibility of pigment.

Further, it is apparent that the reaction products obtained in Production Examples 3 and 4 are improved in the melt viscosity over the reaction products of Production Examples 1 and 2, and the reaction product of Production Example 5 has a even lower viscosity and has excellent properties as a wax for a thermal transfer ink also from the view point of the hue.

Application Examples 1 and 2

A thermal transfer ink prepared to have the composition as shown in Table 2 was applied by hot melt coating on a polyester film having a thickness of 12 μm, in a thickness of 5 μm, whereby a thermal ink transfer recording sheet was obtained. Each sheet obtained in this manner was mounted on a usual thermal facsimile, and thermal recording was conducted on a ordinary paper (a high quality paper, weight: 50 g/m²) by a thermal head, whereby a clear satisfactory printing image was obtained in each case.

Application Example 3

A thermal transfer ink prepared to have the composition as shown in Table 2 was applied by hot melt coating on a polyester film having a thickness of 5 μm, in a thickness of 4 μm, whereby a satisfactory thermal ink transfer recording sheet having no curling or wrinkles was obtained.

This sheet was mounted on a usual thermal facsimile, and thermal recording was conducted on an ordinary paper (high quality paper, weight: 50 g/m²) by a thermal head, wehreby a clear satisfactory printing image was obtained.

TABLE 2

|  | Composition (part by weight) |
|---|---|
| Reaction Product I (Application Example 1), Reaction Product III (Application Example 2) or Reaction Product V (Application Example 3) | 45 |
| Paraffin wax (155° F.) | 45 |
| Carbon Black | 10 |

Application Example 4

A thermal transfer ink was prepared in the same manner as in Application Example 3 except that the alkenyl succinic anhydride-containing composition (Reaction Product V) obtained in Production Example 5 was replaced by the alkenyl succinic anhydride (Reaction Product IV) obtained in Production Example 4. The ink was coated by hot melt coating, whereby wrinkles and curling appeared on the sheet after the coating.

Application Examples 5 and 6

Alkenyl succinic anhydride-containing compositions (Reaction Products VI and VII) having good hues were prepared in the same manner as in Production Example 5 except that the conversion of the maleic anhydride in the thermal addition reaction was changed to 60% and 80% by adjusting the reaction temperature and reaction time. Thermal transfer inks containing Reaction Product VI (Application Example 5) and Reaction Product VII (Application Example 6), respectively, were prepared in the same manner as in Application Example 3, and applied by hot melt coating, whereby satisfactory thermal ink transfer recording sheets were obtained without curling or wrinkles. They were respectively used for the thermal recording in the same manner as in Application Example 3, whereby clear satisfactory printing images were obtained, respectively.

What is claimed is:

1. An ink composition for thermal ink transfer, comprising a pigment and a wax component, wherein said wax component contains a wax which consists essentially of a reaction product of an α-olefin, having an average carbon number of from 16 to 100, with maleic anhydride, said reaction product consisting of one of the formulae:

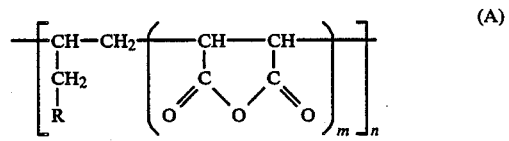

(A)

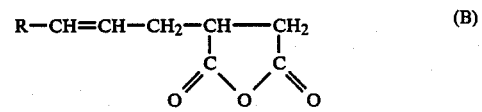

(B)

wherein R is an alkyl group having an average carbon number of from 13 to 97, and m is $\geq 1$, said reaction product having a weight average polymerization degree of from 1 to 100, and a heat of fusion of not higher than 40 cal g$^{-1}$.

2. The ink composition of claim 1, wherein said reaction product is a copolymer of an α-olefin having an average carbon number of from 16 to 60 with maleic anhydride.

3. The ink composition of claim 1, wherein said reaction product is a 1:1 adduct of an α-olefin having an average carbon number of from 16 to 60 with maleic anhydride.

4. The ink composition of claim 1, wherein said reaction product is obtained by subjecting an α-olefin having an average carbon member of from 16 to 100, and maleic anhydride to a thermal addition reaction, followed by a radical reaction with addition of a peroxide.

5. The ink composition of claim 1, comprising 5 to 30% by weight of said pigment and from 70 to 95% by weight of said wax component, wherein at least 5% by weight of said wax component is constituted by said wax.

6. The ink composition of claim 1, wherein said reaction product is a copolymer of an α-olefin having an average carbon number of from 22 to 60, with maleic anhydride.

7. The ink composition of claim 1, wherein said reaction product is a 1:1 adduct of an α-olefin having average carbon number of from 22 to 60 with maleic anhydride.

8. The ink composition of claim 1, wherein said reaction product consists of the formula:

$$\text{(A)}\quad \left[-\text{CH}-\text{CH}_2-\left(-\text{CH}-\text{CH}-\right)_m\right]_n$$
with CH$_2$–R side chain and maleic anhydride ring (O=C–O–C=O).

9. The ink composition of claim 1, wherein said wax contains both reaction products having the formulae:

(A) [as above]

(B) $R-CH=CH-CH_2-CH-CH_2$ with maleic anhydride ring.

10. The ink composition of claim 1, wherein said α-olefin is a mixture of α-olefins having from 16 to 18 carbons.

11. The ink composition of claim 1, wherein said α-olefin is a mixture of α-olefins having from 20 to 28 carbon atoms.

12. The ink composition of claim 1, wherein said α-olefin is a mixture of α-olefins having from 30 to 60 carbon atoms.

13. The ink composition of claim 1, wherein said reaction product is obtained by receiving said α-olefin and said maleic anhydride in a molar ratio of 1:0.5 to 1:2.

14. The ink composition of claim 1, wherein said reaction product is obtained by reacting said α-olefin and said maleic anhydride in a molar ratio of from 1:1 to 1:2.

15. The ink composition of claim 4, wherein said peroxide is di-t-butylperoxide or t-butylhydroperoxide.

16. The ink composition of claim 1, wherein said reaction product has a melting point of from 30° to 95° C.

17. The ink composition of claim 1, wherein said reaction product has a viscosity, at 100° C., of from 10 to 1000 cp.

18. The ink composition of claim 1, wherein said weight average polymerization degree is from 1 to 40.

19. An ink composition for thermal ink transfer, comprising a pigment and a wax component, wherein said wax component contains a wax which consists essentially of a reaction product of an α-olefin, having an average carbon number of from 16 to 100, with maleic anhydride, said reaction product consisting of one of the formulae:

(A) [structure as above]

(B) $R-CH=CH-CH_2-CH-CH_2$ with maleic anhydride ring.

wherein R is an alkyl group having an average carbon number of from 13 to 97, and m is $\geq 1$, said reaction product having a weight average polymerization degree of from 1 to 100, and a heat of fusion of not higher than 40 cal g$^{-1}$;

wherein said wax component comprises from 5 to 100% by weight of said reaction product and up to 95% by weight of a conventional wax comprising paraffin wax, carnauba wax, montan wax, Japan wax, beeswax, ceresin wax, candelilla wax, spermaceti, petroleum wax, low molecular weight polyethylene, or oxidized wax.

20. The ink composition of claim 1, wherein said pigment comprises carbon black.

21. The ink composition of claim 1, wherein said wax component comprises from 10 to 100% by weight of said reaction product and up to 90% by weight of paraffin wax, carnauba wax, montan, Japan wax, beeswax, ceresin wax, candelilla wax, spermaceti, petroleum wax, low molecular weight polyethylene, or oxidized wax.

* * * * *